US 7,122,548 B2

(12) United States Patent
Zhang et al.

(10) Patent No.: US 7,122,548 B2
(45) Date of Patent: Oct. 17, 2006

(54) TRIAZOLOTRIAZINE COMPOUNDS AND USES THEREOF

(75) Inventors: Fang-Jie Zhang, Sunnyvale, CA (US); Tomas Vojkovsky, Boca Raton, FL (US); Ping Huang, Mountain View, CA (US); Congxin Liang, Jupiter, FL (US); Steven Huy Do, San Jose, CA (US); Marcel Koenig, Boca Raton, FL (US); Jingrong Cui, Foster City, CA (US)

(73) Assignee: Sugen, Inc., San Diego, CA (US)

( * ) Notice: Subject to any disclaimer, the term of this patent is extended or adjusted under 35 U.S.C. 154(b) by 0 days.

(21) Appl. No.: 10/874,743

(22) Filed: Jun. 24, 2004

(65) Prior Publication Data

US 2005/0075340 A1 Apr. 7, 2005

Related U.S. Application Data

(60) Provisional application No. 60/484,221, filed on Jul. 2, 2003.

(51) Int. Cl.
*C07D 487/04* (2006.01)
*A61K 31/53* (2006.01)
*A61P 35/00* (2006.01)

(52) U.S. Cl. .................................. 514/243; 544/184
(58) Field of Classification Search ............... 544/184; 514/243

See application file for complete search history.

(56) References Cited

FOREIGN PATENT DOCUMENTS

| EP | 0 662 477 A1 | 7/1995 |
|---|---|---|
| FR | 1.379.480 | 10/1964 |
| GB | 1028809 | 5/1966 |
| GB | 1042471 | 9/1966 |
| WO | WO 83/00864 A1 | 3/1983 |

OTHER PUBLICATIONS

Knudsen et al. Adv Cancer Res. 91: 31–67, 2004.*
Elliott et al. Can. J. Physiol. Pharmacol. 80(2) : 91–102, 2002.*
Futaki et al. Chemical and Pharmaceutical Bulletin 8, 908–912, 1960. CA 55:118573, 1961.*
Cecil Textbook of Medicine, edited by Bennet, J.C., and Plum F., 20th edition,vol. 1, 1004–1010, 1996.*
Gehlen et al., "Reaktionen von 4,5–Diamino–s–triazolen mit Chloressigester und Oxalsäurediäthylester," *Archiv der Pharmazie*, Aug. 1970, pp. 650–656, vol. 8.
Futaki et al., "Studies on the Synthesis of 3–Alkyl–5,6,7, 8-tetrahydro–s–triazolo[4,3–b][1,2,4]triazine–6,7–diones," *Chemical & Pharmaceutical Bulletin*, Oct. 1960, pp. 908–912, vol. 8, No. 10.

Ivanov et al., "Synthesis of Substituted 1,2,4–Triazines based on 1,2–Bis(2,5–Dimethyl–3–Thienyl)Ethanedione," *Chemistry of Heterocyclic Compounds*, Jan. 2001, pp. 85–90, vol. 37, No. 1.
Shaban et al., "Synthesis of acyclo C–nucleosides: 3–(Alditol–1–yl)–6,7–diphenyl–1,2,4–triazolo[4,3–b][1,2, 4]triazines," *Pharmazie*, Oct. 1996, pp. 707–710, vol. 51, No. 10.
Abdel–Rahman et al., "Synthesis of Some New Thioethers of 1,2,4–Triazine–3–Hydrazones and Assays for Their Anticancer and Anti Human Immune Virus Activities," *Il Farmco*, Mar. 1993, pp. 335–446, vol. 48, No. 3.
Zaher et al., "Reactions of 3–Hydrazino–5,6–diphenyl–1,2, 4–triazine with α,β–Bifunctional Compounds," *Indian Journal of Chemistry*, Feb. 1987, pp. 110–115, vol. 26B.
Daunis et al., "C NMR Spectra of s–Triazolo–as–Triazinones: Application to Isomeric and Tautomeric Structure Determination," *Organic Magnetic Resonance*, May 1980, pp. 330–334, vol. 13, No. 5.
Lovell et al., "6– And 7–Aryl–1,2,4–triazolo[4,3–b]–1,2, 4–triazines. Synthesis and Characterization (1)," *Journal of heterocyclic Chemistry*, Nov. 1979, pp. 1393–1403, vol. 16, No. 7.
Daunis et al., "Synthese et reactivite de dihydrotriazines et de dihydrotriazolotriazines," *Journal of Heterocyclic Chemistry*, Apr. 1979, pp. 427–432, vol. 16, No. 3, HeteroCorporation.
Zaher et al., "Uncondensed 1,2,4–Triazines: Part I—Behaviour of 3–Hydrazino–5,6–diphenyl–1,2,4–triazine Towards Acylating Agents, Acitivated Alkenes & Carbonyl Compounds," *Indian Journal of Chemistry*, Oct. 1979, pp. 316–319, vol. 18B.
Daunis et al., "Heteroaromatic 10–π–Electron Systems. New s–Triazolo–as–triazines with a Bridgehead Nitrogen Atom," *J. Org. Chem.*, 1977, pp. 1018–1022, vol. 42, No. 6.
Daunis et al., "Fragmentations Principales de Mono–, Di–, Tri– et Tetra –azaindolizines Sous L'Impact Electronique," *Organic Mass Spectrometry*, 1977, pp. 739–745, vol. 12, No. 12.

(Continued)

*Primary Examiner*—Venkataraman Balasubramanian
(74) *Attorney, Agent, or Firm*—Bryan C. Zielinski; Vincent P. Liptak

(57) ABSTRACT

The present invention relates to compounds of the Formula (I), and their pharmaceutically acceptable salts. These compounds modulate the activity of c-Met and are therefore expected to be useful in the prevention and treatment of c-Met related disorders such as cancer 13 Claims, No Drawings

OTHER PUBLICATIONS

Daunis et al., "Etude en serie as–triazine. XVIII.—Etude de la tautomerie de triazolo–triazinones," *Bulletin de la Societe Chimique de France*, Jul.–Aug. 1976, pp. 1178–1182, No. 7–8.

Daunis et al., "Etude En Serie as–Triazine, XIX—Fragmentations Principales de s–Triazolo–as Triazinones en Spectrometrie de Masse," *Organic Mass Spectrometry*, 1976, pp. 752–762, vol. 11.

Daunis et al., "Etude en serie as–triazine. XCI.—Effet du substituant situe en position 6 des hydrazine–3 hydroxy–5 triazines sur l'oreintation de la cyclisation en s–triazolo as–triazine," *Bulletin de la Societe Chimique de France*, Mar.–Apr. 1975, pp. 857–863.

Daunis et al., "Etude en serie as–Triazine. II.—Syntheses et transpositions de s–Triazolo–as–Triazine," *Bulletin de la Societe Chimique de France*, 1969, pp. 2492–2501, No. 7.

Kalfus, "Ionisation Einiger 1,2,4–Triazine," *Collection Czechoslov. Chem. Commun.*, 1968, pp. 2962–2969, vol. 33.

Kalfus, "3–Hydrazino–1,2,4–Triazines," *Collection Czechoslov. Chem. Commun.*, 1968, pp. 2513–2517, vol. 33.

Katsumura et al., "Organic Tin Compounds. V. Uses," *Kagaku no Ryoiki*, 1964, pp. 1062–1068, vol. 18, No. 12.

Kijima, "Organic Tin Compounds. IV. Reactions," *Kagaku no Ryoiki*, 1964, pp. 1058–1062, vol. 18, No. 12.

Tanaka, "5. Alkyltin Chelates," *Kagaku no Ryoiki*, 1964, pp. 1055–1057, vol. 18, No. 12.

Okawara, "4. Monoalkyltin Derivatives," *Kagaku no Ryoiki*, 1964, p. 1055, vol. 18, No. 12.

Wada, "3. Dialkyltin Derivatives," *Kagaku no Ryoiki*, 1964, pp. 1052–1055, vol. 18, No. 12.

Kasai, "2. Trialkyltin Derivatives," *Kagaku no Ryoiki*, 1964, pp. 1046–1052, vol. 18, No. 12.

Daunis et al., "Synthesis and Reactivity of Dihydrotriazines and Dihydrotriazolotriazines," *Journal of Heterocyclic Chemistry*, Apr. 1979, pp. 427–432, vol. 16.

Daunis et al., "Principal Fragmentations of Mono–azaindolizines, Di–azaindolizines, Tri–azaindolizines and Tetra–azaindolizines under Electronic Impact," *Organic Mass Spectrometry*, Dec. 1977, pp. 739–745, vol. 12, No. 12.

D'Alo et al., "Synthesis of a new polyazotized tricyclic system," *Annali Di Chimica*, Apr. 1967, pp. 366–375, vol. 57.

Daunis et al., "Study on the as–Triazine Series, II. Syntheses and Transposition of s–Triazolo–as–Triazine," 1969, pp. 2492–2501.

Database Caplus Accession No. 1961:118573, 1961. Futaki et al., Synthesis of 3–alkyl–5,6,7,8–tetrahydro–s–triazolo[4,3–b][1,2,4]triazine–6,7–diones. Chemical & Pharmaceutical Bulletin 8, 908–91, 1960.

* cited by examiner

TRIAZOLOTRIAZINE COMPOUNDS AND USES THEREOF

This application claims the benefit of U.S. Provisional Application Ser. No. 60/484,221, filed Jul. 2, 2003, the disclosure of which is incorporated herein by reference in its entirety.

BACKGROUND OF THE INVENTION

The following is offered as background information only and is not admitted to be prior art to the present invention.

Protein kinases ("PKs") are enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer).

The PKs can be conveniently broken down into two classes, the protein tyrosine kinases (PTKs) and the serine-threonine kinases (STKs).

One of the prime aspects of PTK activity is their involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger and Ullrich, *Neuron* 9:303–391 (1992), which is incorporated by reference, including any drawings, as if fully set forth herein.

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR (epithelial growth factor receptor), HER2, HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated subunits and two subunits which cross the cell membrane and which contain the tyrosine kinase domain.

A third RTK subfamily is referred to as the platelet derived growth factor receptor ("PDGFR") group, which includes PDGFR, PDGFR, CSFIR, c-kit and c-fms. These receptors consist of glycosylated extracellular domains composed of variable numbers of immunoglobin-like loops and an intracellular domain wherein the tyrosine kinase domain is interrupted by unrelated amino acid sequences.

Another group which, because of its similarity to the PDGFR subfamily, is sometimes subsumed into the later group is the fetus liver kinase ("flk") receptor subfamily. This group is believed to be made of up of kinase insert domain-receptor fetal liver kinase-1 (KDR/FLK-1), flk-1R, flk-4 and fms-like tyrosine kinase 1 (flt-1). Still another member of the growth factor receptor family is the vascular endothelial growth factor ("VEGF") receptor subgroup. VEGF is a dimeric glycoprotein similar to PDGF but has different biological functions and target cell specificity in vivo. In particular, VEGF is presently thought to play an essential role is vasculogenesis and angiogenesis.

A further member of the tyrosine kinase growth factor receptor family is the fibroblast growth factor ("FGF") receptor subgroup. This group consists of four receptors, FGFR1–4, and seven ligands, FGF1–7. While not yet well defined, it appears that the receptors consist of a glycosylated extracellular domain containing a variable number of immunoglobin-like loops and an intracellular domain in which the tyrosine kinase sequence is interrupted by regions of unrelated amino acid sequences.

Still another member of the tyrosine kinase growth factor receptor family is MET, often referred to as c-Met. c-met is also known as hepatocyte growth factor receptor or scatter factor receptor. c-Met is thought to play a role in primary tumor growth and metastasis.

A more complete listing of the known RTK subfamilies is described in Plowman et al., *DN&P*, 7(6):334–339 (1994), which is incorporated by reference, including any drawings, as if fully set forth herein.

In addition to the RTKs, there also exists a family of entirely intracellular PTKs called "non-receptor tyrosine kinases" or "cellular tyrosine kinases." This latter designation, abbreviated "CTK," will be used herein. CTKs do not contain extracellular and transmembrane domains. At present, over 24 CTKs in 11 subfamilies (Src, Frk, Btk, Csk, Abl, Zap70, Fes, Fps, Fak, Jak and Ack) have been identified. The Src subfamily appear so far to be the largest group of CTKs and includes Src, Yes, Fyn, Lyn, Lck, Blk, Hck, Fgr and Yrk. For a more detailed discussion of CTKs, see Bolen, *Oncogene*, 8:2025–2031 (1993), which is incorporated by reference, including any drawings, as if fully set forth herein.

The serine/threonine kinases, STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes.

RTKs, CTKs and STKs have all been implicated in a host of pathogenic conditions including, significantly, cancer. Other pathogenic conditions which have been associated with PTKs include, without limitation, psoriasis, hepatic cirrhosis, diabetes, angiogenesis, restenosis, ocular diseases, rheumatoid arthritis and other inflammatory disorders, immunological disorders such as autoimmune disease, cardiovascular disease such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

In view of the apparent link between PK-related cellular activities and wide variety of human disorders, it is no surprise that a great deal of effort is being expended in an attempt to identify ways to modulate PK activity. Some of these have involved biomimetic approaches using large molecules patterned on those involved in the actual cellular processes (e.g., mutant ligands (U.S. application Ser. No. 4,966,849); soluble receptors and antibodies (Application No. WO 94/10202, Kendall and Thomas, *Proc. Nat'l Acad. Sci.*, 90:10705–10709 (1994), Kim, et al., *Nature*, 362:841–844 (1993)); RNA ligands (Jelinek, et al., *Biochemistry*, 33:10450–56); Takano, et al., *Mol. Bio. Cell*, 4:358A (1993); Kinsella, et al., *Exp. Cell Res.*, 199:56–62 (1992); Wright, et al., *J. Cellular Phys.*, 152:448–57) and tyrosine kinase inhibitors (WO 94/03427; WO 92/21660; WO 91/15495; WO 94/14808; U.S. Pat. No. 5,330,992; Mariani, et al., *Proc. Am. Assoc. Cancer Res.*, 35:2268 (1994)).

In addition to the above, attempts have been made to identify small molecules which act as PK inhibitors. For example, bis-monocyclic, bicyclic and heterocyclic aryl compounds (PCT WO 92/20642), vinylene-azaindole derivatives (PCT WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP Application No. 0 566 266 A1), selenaindoles and selenides (PCT WO 94/03427), tricyclic polyhydroxylic compounds (PCT WO 92/21660) and benzylphosphonic acid compounds (PCT WO 91/15495) have all been described as PTK inhibitors useful in the treatment of cancer.

SUMMARY OF THE INVENTION

A family of novel triazolotriazine compounds have been discovered which exhibit c-Met modulating ability and have a ameliorating effect against disorders related to abnormal c-Met activity. c-Met is an attractive target from a clinical perspective because: 1) c-Met has been implicated in the growth and metastases of most types of cancer; 2) growth at the secondary site appears to be the rate-limiting step in metastasis; and 3) by the time of diagnosis, it is likely that the disease has already spread.

c-Met is a receptor tyrosine kinase that is encoded by the Met protooncogene and transduces the biological effects of hepatocyte growth factor (HGF), which is also referred to as-scatter factor (SF). Jiang et al., *Crit. Rev. Oncol. Hematol.* 29: 209–248 (1999). c-Met and HGF are expressed in numerous tissues, although their expression is normally confined predominantly to cells of epithelial and mesenchymal origin, respectively. c-Met and HGF are required for normal mammalian development and have been shown to be important in cell migration, cell proliferation and survival, morphogenic differentiation, and organization of 3-dimensional tubular structures (e.g., renal tubular cells, gland formation, etc.). It is proposed that c-Met-dependent tumor growth, invasion, and dissemination is mediated by these cellular actions. In addition to its effects on epithelial cells, HGF/SF has been reported to be an angiogenic factor, and c-Met signaling in endothelial cells can induce many of the cellular responses necessary for angiogenesis (proliferation, motility, invasion).

The c-Met receptor has been shown to be expressed in a number of human cancers. c-Met and its ligand, HGF, have also been shown to be co-expressed at elevated levels in a variety of human cancers (particularly sarcomas). However, because the receptor and ligand are usually expressed by different cell types, c-Met signaling is most commonly regulated by tumor-stroma (tumor-host) interactions. Furthermore, c-Met gene amplification, mutation, and rearrangement have been observed in a subset of human cancers. Families with germlne mutations that activate c-Met kinase are prone to multiple kidney tumors as well as tumors in other tissues. Numerous studies have correlated the expression of c-Met and/or HGF/SF with the state of disease progression of different types of cancer (including lung, colon, breast, prostate, liver, pancreas, brain, kidney, ovaries, stomach, skin, and bone cancers). Furthermore, the overexpression of c-Met or HGF have been shown to correlate with poor prognosis and disease outcome in a number of major human cancers including lung, liver, gastric, and breast. The strong correlation of c-Met with the biology of metastasis and invasion and disease pathogenesis comprises a novel mechanism for treatment of metastatic cancers.

c-Met has been directly implicated in cancers without a successful treatment regimen such as pancreatic cancer, glioma, and hepatocellular carcinoma. A c-Met kinase inhibitor could fill an unmet medical need in the treatment of these cancers.

These observations suggest that c-Met kinase inhibitors would be an effective treatment for primary tumors that are driven by c-Met, but more importantly, would prevent disseminated micrometastases from growing into life-threatening metastases. Therefore, the utility of a c-Met inhibitor extends to preventative and adjuvant therapy settings. In addition, certain cancers (e.g., papillary renal cell carcinoma, some gastric and lung cancers) can be treated which are believed to be driven by c-Met mutation/genetic alteration and dependent on c-Met for growth and survival. These cancers are expected to be sensitive to treatment.

Various human cancers are the primary target indication for c-Met antagonists. These cancers include major cancers such as breast, lung, colorectal, prostate; as well as pancreatic cancer, glioma, liver cancer, gastric cancer, head and neck cancers, melanoma, renal cancer, leukemias, myeloma, and sarcomas.

The compounds presented herein are exemplary only and are not to be construed as limiting the scope of this invention in any manner.

In one embodiment, the invention is directed to compounds of Formula (I), or a pharmaceutically acceptable salt thereof.

Formula (I) is represented as follows:

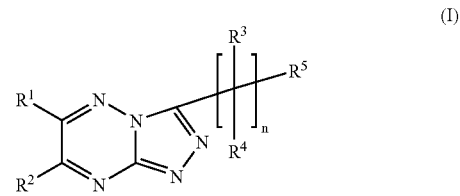

wherein
n is 1, 2 or 3;

R¹ is selected from the group consisting of hydrogen, halogen, —OH, —OR⁶, NR⁶R⁷, —CN, —COR⁶, —COOR⁶, —CONR⁶R⁷, perfluoroalkyl, $C_1$–$C_6$ alkyl, cycloalkyl, heterocycle, alkenyl, alkynyl, aryl, and heteroaryl, wherein the $C_1$–$C_6$ alkyl, cycloalkyl, heterocycle, alkenyl, alkynyl, aryl or heteroaryl of R¹ maybe be optionally and independently substituted with one or more of halogen, —OH, —OR⁶, —COR⁷, —CONR⁶R⁷, —COOR⁶, —NR⁶R⁷, —CN, —NO₂, —NO₂, —S(O)R⁶, (m=0, 1 (m=0.1 or 2), —S(O₂)NR⁶R⁷, —NR⁶ R⁷, perfluoroalkyl, $C_1$–$C_6$ alkyl, cycloalkyl, heterocycle, $C_1$–$C_6$ alkenyl, $C_1$–$C_6$ alkynyl, aryl, heteroaryl, —NR⁶ONR⁶R⁷, —NR⁶OR⁷ and —NR⁶S(O₂)R⁷;

R² is selected from the group consisting of hydrogen, —OH, halogen, $C_1$–$C_6$ alkyl, —OR⁸, NR⁸R⁹, —CN, —COR⁸, —COOR⁹, —CONR⁸R⁹, and perfluoroalkyl, each R³ and R⁴ is independently selected from the group consisting of hydrogen, halogen, —OH, —OR⁶, —NR⁶R⁷, —CN, —COR⁶, —COOR⁶, —CONR⁶R⁷, —NR⁶ R⁷ perfluoroalkyl, $C_1$–$C_6$ alkyl, aryl, cycloaryl, heterocycle and heteroaryl;

R⁵ is aromatic ring or heteroaromatic ring, wherein R⁵ is optionally substituted at one or more positions with halogen, —OH, —OR⁶, —COR⁷, —CONR⁶R⁷, —COOR⁶, —NR⁶R⁷, —CN, —NO₂, —S(O)ₘR⁶, (m=0, 1 or 2), —S(O₂)NR⁶R⁷, —NR⁶R⁷, perfluoroalkyl or $C_1$–$C_6$ alkyl;

each R⁶ and R⁷ is independently hydrogen, $C_1$–$C_6$ alkyl, cycloalkyl, heterocyclic, alkenyl, alkynyl, aryl, aminoalkyl, alkylaminoalkyl, or dialkylaminoalkyl; and each R⁸ and R⁹ is independently hydrogen or $C_1$–$C_6$ alkyl;

or a pharmaceutically acceptable salt thereof.

In a particular aspect of this embodiment, R₁ is aryl or heteroaryl, wherein the aryl or heteroaryl may be optionally substituted at one or more positions with halogen, —OH, —OR⁶, —COR⁷, —CONR⁶R⁷, —COOR⁶, —NR⁶R⁷, —CN, —NO₂, —S(O)ₘR⁶, (m=0, 1 or 2), —S(O₂)NR⁶R⁷ˢ, —NR⁶R⁷, perfluoroalkyl, $C_1$–$C_6$ alkyl, cycloalkyl, heterocycle, $C_1$–$C_6$ alkenyl, $C_1$–$C_6$ alkynly, aryl heteroaryl, —NR⁶ONR⁶R⁷, —NR⁶OR⁷ or —NR⁶S(O₂)R⁷, wherein the aryl or heteroaryl is a five or six membered ring.

In another particular aspect of this embodiment, and in combination with any other particular aspect not inconsistent, R² is H or $C_1$–$C_4$ alkyl, preferably H.

In another particular aspect of this embodiment, and in combination with any other particular aspect not inconsistent, R⁵ is a 6 membered aryl or heteroaryl ring, wherein the 6 membered heteroaryl ring can be substituted within the ring with one or more members independently selected from the group consisting of S, O and N.

In another particular aspect of this embodiment, and in combination with any other particular aspect not inconsistent, R⁵ is a 6 membered heteroaryl ring selected from pyranyl, pyridyl, pyrazinyl, pyrimidinyl, or pyridazinyl.

In another particular aspect of this embodiment, and in combination with any other particular aspect not inconsistent, R⁵ is phenyl, which can be optionally substituted with hydroxy or halo.

In another particular aspect of this embodiment, and in combination with any other particular aspect not inconsistent, n is 1 or 2.

In another embodiment, the invention provides compounds of formula Ia

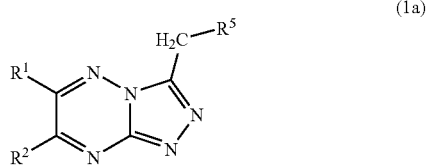

(1a)

wherein

R¹ is selected from the group consisting of hydrogen, halogen, —OH, —OR⁶, NR⁶R⁷, —CN, —COR⁶, —COOR⁶, —CONR⁶R⁷, perfluoroalkyl, $C_1$–$C_6$ alkyl, cycloalkyl, heterocycle, alkenyl, alkynyl, aryl, and heteroaryl, wherein the $C_1$–$C_6$ alkyl, cycloalkyl, heterocycle, alkenyl, alkynyl, aryl or heteroaryl of R¹ maybe be optionally and independently substituted with one or more of halogen, —OH, —OR⁶, —COR, —CONR⁶R⁷, —COOR⁶, —NR⁶R⁷, —CN, —NO₂, —S(O)ₘR⁶, (m=0,1 or 2), —S(O₂)NR⁶R⁷, —NR⁶ R⁷, perfluoroalkyl, $C_1$–$C_6$ alkyl, cycloalkyl, heterocycle, $C_{1-6}$ alkenyl, $C_1C_6$ alkynyl, aryl, heteroaryl, —NR⁶ONR⁶R⁷, —NR⁶OR⁷ and —NR⁶S(O₂)R⁷;

R² is selected from the group consisting of hydrogen, —OH, halogen, $C_1$–$C_6$ alkyl, —OR⁸, NR⁸R⁹, —CN, —COR⁸, —COOR⁹, —CONR⁸R⁹, and perfluoroalkyl, R⁵ is aromatic ring or heteroaromatic ring, wherein R⁵ may be optionally substituted at one or more positions with halogen, —OH, —OR⁶, —COR⁷, —CONR⁶R⁷, —COOR⁶, —NR⁶R⁷—CN, —NO₂, —S(O)ₘR⁶, (m=0, 1 or 2), —S(O₂)NR⁶R⁷, —NR⁶R⁷, perfluoroalkyl or $C_1$–$C_6$ alkyl;

each R⁶ and R⁷ is independently hydrogen, $C_1$–$C_6$ alkyl, cycloalkyl, heterocyclic, alkenyl, alkynyl, aryl, aminoalkyl, alkylaminoalkyl, and dialkylaminoalkyl; and each R⁸ and R⁹ is independently hydrogen or $C_1$–$C_6$ alkyl;

or a pharmaceutically acceptable salt thereof.

In a particular aspect of this embodiment, R₁ is aryl or heteroaryl, wherein the aryl or heteroaryl may be optionally substituted at one or more positions with halogen, —OH, —OR⁶, —COR⁷, —CONR⁶R⁷, —COOR⁶, —NR⁶R⁷, —CN, —NO₂, —S(O)ₘR⁶, (m=0,1 or 2), —S(O₂)NR⁶R⁷ˢ, —NR⁶R⁷, perfluoroalkyl, $C_1$–$C_6$ alkyl, cycloalkyl, heterocycle, $C_1$–$C_6$ alkenyl, $C_1$–$C_6$ alkynyl, aryl heteroaryl, —NR⁶ONR⁶R⁷, —NR⁶OR⁷ or —NR⁶S(O₂)R⁷, wherein the aryl or heteroaryl is a five or six membered ring.

In another particular aspect of this embodiment, and in combination with any other particular aspect not inconsistent, R² is H or $C_1$–$C_4$ alkyl, preferably H.

In another particular aspect of this embodiment, and in combination with any other particular aspect not inconsistent, R⁵ is a 6 membered aryl or heteroaryl ring, wherein the 6 membered heteroaryl ring can be substituted within the ring with one or more members independently selected from the group consisting of S, O and N.

In another particular aspect of this embodiment, and in combination with any other particular aspect not inconsistent, R⁵ is a 6 membered heteroaryl ring selected from pyranyl, pyridyl, pyrazinyl, pyrimidinyl, or pyridazinyl.

In another embodiment, the invention provides a compound selected from the group consisting of

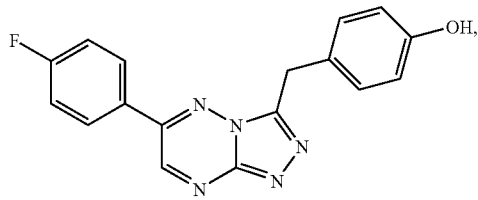

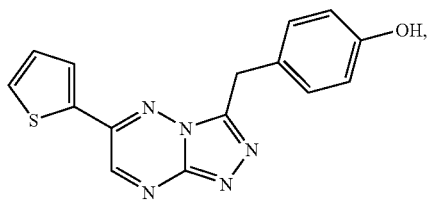

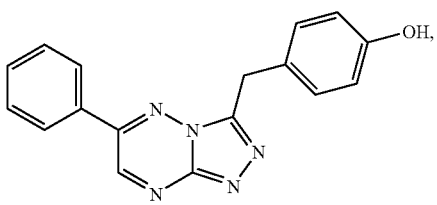

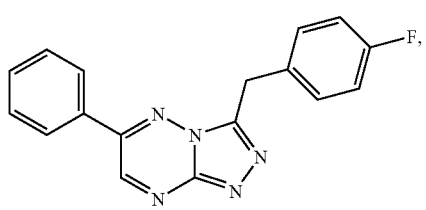

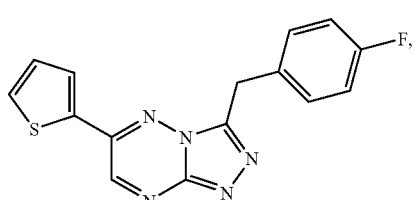

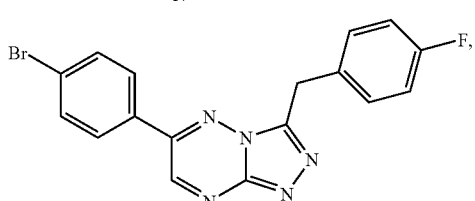

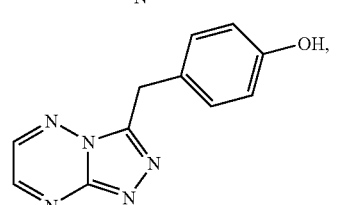

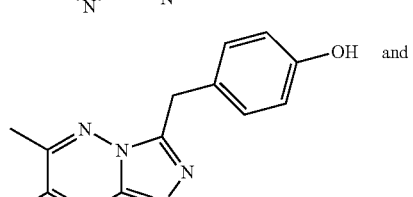 and

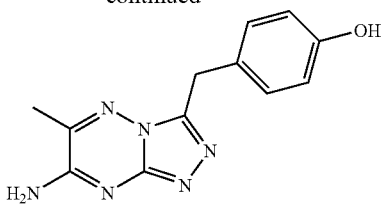

or a pharmaceutically acceptable salt thereof.

Any of the compounds of the present invention may be present in a pharmaceutical composition with a pharmaceutically acceptable carrier.

Another aspect of the present invention is a method for treating a c-Met related disorder by administering to an organism in need thereof a therapeutically effective amount of a compound of the present invention.

In particular, the a c-Met related disorder can be cancer, such as breast cancer, lung cancer, colorectal cancer, prostate cancer, pancreatic cancer, glioma, liver cancer, gastric cancer, head cancer, neck cancer, melanoma, renal cancer, leukemia, myeloma, and sarcoma.

Specific examples of compounds of Formula I are described in Table 2, attached hereto.

It is also an aspect of this invention that a compound described herein, or its salt, might be combined with other chemotherapeutic agents for the treatment of the diseases and disorders discussed above. For instance, a compound or salt of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Likewise a compound or salt of this invention might be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

A compound or salt of this invention might also be expected to prove efficacious in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound or salt of this invention might be expected to have a beneficial effect used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors (such as anastrozole.

Finally, the combination of a compound of this invention might be expected to be particularly effective in combination with mitoxantrone or paclitaxel for the treatment of solid tumor cancers or leukemias such as, without limitation, acute myelogenous (non-lymphocytic) leukemia.

The above method can be carried out in combination with a chemotherapeutic agent selected from the group consisting of mitotic inhibitors, alkylating agents, antimetabolites, cell cycle inhibitors, enzymes, topoisomerase inhibitors, biological response modifiers, anti-hormones, antiangiogenic agents such as MMP-2, MMP-9 and COX-2 inhibitors, and anti-androgens.

Examples of useful COX-II inhibitors include Vioxx™, CELEBREX™ (alecoxib), valdecoxib, paracoxib, rofecoxib, and Cox 189. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference.

Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32–3555, RS 14–0830, and the compounds recited in the following list:

3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylam ino]-8-oxa-bicyclo[3.2.1]octane-3-carboxylic acid hydroxyamide; (2R, 3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylam ino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R, 3R) 1-[4-(4-fluoro-2-methyl-benzyloxy)-benzenesulfonyl]-3-hydroxy-3-methyl-piperidine-2-carboxylic acid hydroxyamide; 3-[[(4-(4-fluoro-phenoxy)-benzenesulfonyl]1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2. 1]octane-3-carboxylic acid hydroxyamide; 3-endo-3-[4-(4-fluoro-phenoxy)-benzenesulfonylamino]-8-oxa-bicyclo[3.2. 1]octane-3-carboxylic acid hydroxyamide; and (R) 3-[4-(4-fluoro-phenoxy)-benzenesulfonylam ino]-tetrahydro-furan-3-carboxylic acid hydroxyamide; and pharmaceutically acceptable salts and solvates of said compounds.

Other anti-angiogenesis agents, including other COX-II inhibitors and other MMP inhibitors, can also be used in the present invention.

Compounds of Formula (I) can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN.™. (Genentech, Inc. of South San Francisco, Calif., USA). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

These and other EGFR-inhibiting agents can be used in the present invention.

VEGF inhibitors, for example SU-5416, SU 11248, SU-6668 (Sugen Inc. of South San Francisco, Calif., USA), can also be combined with a compounds of Formula (I). VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 01/60814,WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun.26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with a compounds of Formula (I) for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27,1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with compounds of Formulae (I) and (III)–(XII), in accordance with the present invention.

Compounds of Formula (I) can also be used with other agents useful in treating cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No, 6,258,824 B1. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

The above method can be also be carried out in combination with radiation therapy, wherein the amount of a compound of Formula (i) in combination with the radiation therapy, is effective in treating the above diseases. The level of radiation therapy administered may be reduced to a sub-efficacy dose when administered in combination with the compounds of the preferred embodiments of the present invention.

Techniques for administering radiation therapy are known in the art, and these techniques can be used in the combination therapy described herein. The administration of the compound of the invention in this combination therapy can be determined as described herein.

Another aspect of the invention is directed to the use of compounds of the Formula (I) in the preparation of a medicament, which is useful in the treatment of a disease mediated by abnormal Met kinase activity.

"Pharmaceutically acceptable salt" or "pharmaceutically acceptable salt thereof" refer to those salts which retain the biological effectiveness and properties of the free bases and which are obtained by reaction with inorganic or organic acids, such as hydrochloric acid, hydrobromic acid, hydroiodic acid, sulfuric acid, nitric acid, phosphoric acid, methanesulfonic acid, ethanesulfonic acid, p-toluenesulfonic acid, salicylic acid, acetic acid, benzenesulfonic acid (besylate), benzoic acid, camphorsulfonic acid, citric acid, fumaric acid, gluconic acid, glutamic acid, isethionic acid, lactic acid, maleic acid, malic acid, mandelic acid, mucic acid, pamoic acid, pantothenic acid, succinic acid, tartaric acid, and the like.

A "pharmaceutical composition" refers to a mixture of one or more of the compounds described herein, or physiologically acceptable salts thereof, with other chemical components, such as physiologically acceptable carriers and excipients. The purpose of a pharmaceutical composition is to facilitate administration of a compound to an organism.

As used herein, a "physiologically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives (including microcrystalline cellulose), gelatin, vegetable oils, polyethylene glycols, diluents, granulating agents, lubricants, binders, disintegrating agents, and the like.

"Alkyl" refers to a saturated aliphatic hydrocarbon including straight chain, branched chain or cyclic groups. Preferably, the alkyl group has 1 to 20 carbon atoms (whenever a numerical range; e.g., "1–20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, each substituent group is preferably one or more individually selected from halogen, -hydroxy, —COR', —COOR', OCOR', —CONRR', —RNCOR ', —NRR', —CN, —NO$_2$, —CZ$_3$, —SR', —SOR', —SO$_2$R', —SO$_2$OR', —SO$_2$ NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' are independently H, alkyl, or aryl, wherein alkyl or aryl may be further substituted with halogen, (CH$_2$)$_n$N(R")$_2$, (CH$_2$)$_n$CO$_2$R", (CH$_2$)$_n$OR", (CH$_2$)$_n$OC(O)R", alkoxycarbonyl, aryloxycarbonyl, aminocarbonyl, a heteroalicyclic ring, aryl, alkoxy, —OCZ$_3$, aryloxy, C(O)NH$_2$ or heteroaryl. R" is H, alkyl or aryl. n is 0–3.

"Alkenyl" refers to an aliphatic hydrocarbon having at least one carbon-carbon double bond, including straight chain, branched chain or cyclic groups having at least one carbon-carbon double bond. Preferably, the alkenyl group has 2 to 20 carbon atoms (whenever a numerical range; e.g., "2–20", is stated herein, it means that the group, in this case the alkenyl group, may contain 2 carbon atoms, 3 carbon atoms, etc. up to and including 20 carbon atoms). More preferably, it is a medium size alkenyl having 2 to 10 carbon atoms. Most preferably, it is a lower alkenyl having 2 to 6 carbon atoms. The alkenyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

"Alkynyl" refers to an aliphatic hydrocarbon having at least one carbon-carbon triple bond, including straight chain, branched chain or cyclic groups having at least one carbon-carbon triple bond. Preferably, the alkenyl group has 2 to 20 carbon atoms (whenever a numerical range; e.g., "2–20", is stated herein, it means that the group, in this case the alkynyl group, may contain 2 carbon atoms, 3 carbon atoms, etc. up to and including 20 carbon atoms). More preferably, it is a medium size alkynyl having 2 to 10 carbon atoms. Most preferably, it is a lower alkynyl having 2 to 6 carbon atoms. The alkynyl group may be substituted or unsubstituted. When substituted, each substituent group is preferably one or more individually selected from halogen, -hydroxy, —COR', —COOR', OCOR', —CONRR', —RNCOR ', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

A "cycloalkyl" or an "alicyclic" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, adamantane, cyclohexadiene, cycloheptane and, cycloheptatriene. A cycloalkyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, each substituted group is preferably one or more selected halogen, hydroxy, alkoxy, aryloxy,—COR', —COOR', OCOR', —CONRR', —RNCOR', —NRR', —CN, —NO$_2$, —CZ$_3$, —OCZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, each substituted group is preferably one or more selected from halogen, -hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalky, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl, where Z is halogen. Wherein R and R' are defined herein.

A "heteroalicyclic ring" or "heteroalicycle" group refers to a monocyclic or fused ring group having in the ring(s) one or more atoms selected from the group consisting of nitrogen, oxygen and sulfur. The rings may also have one or more double bonds. However, the rings may not have a completely conjugated pi-electron system. The heteroalicyclic ring may be substituted or unsubstituted. The heteroalicyclic ring may contain one or more oxo groups. When substituted, the substituted group(s) is preferably one or more selected halogen, hydroxy, —COR', —COOR', OCOR', —CONRR', —RNCOR', —NRR', —CN, —NO$_2$, —CZ$_3$, —SR', —SOR ', —SO$_2$R', —SO$_2$OR', —SO$_2$NRR', thiocarbonyl, —RNSO$_2$R', perfluoroalkyl, O-carbamyl, N-carbamly O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

Z refers to a halogen group selected from the group consisting of fluorine, chlorine, bromine and iodine.

A "hydroxy" group refers to an —OH group.

An "alkoxy" group refers to both an —O-alkyl and an —O-cycloalkyl group, as defined herein.

An "alkoxycarbonyl" refers to a —C(O)—OR.

An "aminocarbonyl" refers to a —C(O)—NRR'.

An "aryloxycarbonyl" refers to —C(O)-O aryl.

An "aryloxy" group refers to both an —O-aryl and an —O-heteroaryl group, as defined herein.

An "arylalkyl" group refers to —alkyl-aryl, where alkyl and aryl are defined herein.

An "arylsulfonyl"group refers to a —SO$_2$-aryl.

An "alkylsulfonyl" group refer to a —SO$_2$-alkyl.

A "heteroaryloxyl" group refers to a heteroaryl-O— group with heteroaryl as defined herein.

A "heteroalicycloxy" group refers to a heteroalicyclic-O— group with heteroalicyclic as defined herein.

A "carbonyl" group refers to a —C(=O)—R.

An "aldehyde" group refers to a carbonyl group where R is hydrogen.

A "thiocarbonyl" group refers to a —C(=S)—R group.

A "trihalomethanecarbonyl" group refers to a Z$_3$C—C(O)— group.

A "C-carboxyl" group refers to a —C(O)O—R groups.

An "O-carboxyl" group refers to a R—C(O)O— group.

A "carboxylic acid" group refers to a C-carboxyl group in which R is hydrogen.

A "halo" or "halogen" group refers to fluorine, chlorine, bromine or iodine.

A "trihalomethyl" group refers to a —CZ$_3$ group.

A "trihalomethanesulfonyl" group refers to a $Z_3CS(O)_2$ group.

A "trihalomethanesulfonamido" group refers to a $Z_3CS(O)_2NR$— group.

A "sulfinyl" group refers to a —S(O)R group.

A "sulfonyl" group refers to a —S(O)$_2$R group.

An "S-sulfonamido" group refers to a —S(O)$_2$NRR' group.

An "N-Sulfonamido" group refers to a —NR—S(O)$_2$R group.

An "O-carbamyl" group refers to a —OC(O)NRR' group.

An "N-carbamyl" group refers to a ROC(O)NR— group.

An "O-thiocarbamyl" group refers to a —OC(S)NRR' group.

An "N-thiocarbamyl" group refers to a ROC(S)NR'— group.

An "amino" group refers to an —NH$_2$ or an —NRR' group.

A "C-amido" group refers to a —C(O)NRR' group.

An "N-amido" group refers to a R'C(O)NR— group.

A "nitro" group refers to a —NO$_2$ group.

A "cyano" group refers to a —CN group.

A "silyl" group refers to a —Si(R)$_3$ group.

A "phosphonyl" group refers to a P(=O)(OR)$_2$ group.

An "aminoalkyl" group refers to an -alkylNRR' group.

An "alkylaminoalkyl" group refers to an -alkyl—NR—alkyl group.

A "dialkylaminoalkyl" group refers to an -alkyl—N—(alkyl)$_2$ group.

A "perfluoroalkyl group" refers to an alkyl group where all of the hydrogen atoms have been replaced with fluorine atoms.

The definitions of $R_1$–$R_{68}$, A, B, X, Y, G, L, R, R' and R" are defined in the present specification.

Compounds that have the same molecular formula but differ in the nature or sequence of bonding of their atoms or arrangements of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". The chemical formulae referred to herein may exhibit the phenomena of tautomerism and structural isomerism. This invention encompasses any tautomeric or structural isomeric form and mixtures thereof which possess the ability to modulate c-Met activity and is not limited to any one tautomeric or structural isomeric form. This invention encompasses any tautomeric or structural isomeric form and mixtures thereof which possess the ability to modulate c-Met activity and is not limited to any one tautomeric or structural isomeric form.

The compounds of this invention may possess one or more asymmetric centers; such compounds can therefore be produced as individual (R)- or (S)-stereoisomers or as mixtures thereof. For example, if the $R^3$ and $R^4$ substituents in a compound of Formula (I) are different, then that carbon is an asymmetric center. Thus, the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992). Thus, this invention also encompasses any stereoisomeric form, their corresponding enantiomers (d- and l- or (+) and (−) isomers) and diastereomers thereof, and mixtures thereof, which possess the ability to modulate c-Met activity and is not limited to any one stereoisomeric form.

The compounds of Formula (I) or (Ia) may exhibit the phenomena of tautomerism and structural isomerism. This invention encompasses any tautomeric or structural isomeric form and mixtures thereof which possess the ability to modulate c-Met activity and is not limited to any one tautomeric or structural isomeric form.

It is contemplated that compounds of the Formulae (I) or (Ia) would be metabolized by enzymes in the body of the organism such as human being to generate a metabolite that can modulate the activity of c-Met. Such metabolites are within the scope of the present invention.

The term "method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

As used herein, the term "modulation" or "modulating" refers to the alteration of the catalytic activity of c-Met. In particular, modulating refers to the activation of the catalytic activity of c-Met, preferably the activation or inhibition of the catalytic activity of c-Met, depending on the concentration of the compound or salt to which c-Met is exposed or, more preferably, the inhibition of the catalytic activity of c-Met.

The term "contacting" as used herein refers to bringing a compound of this invention and c-Met together in such a manner that the compound can affect the catalytic activity of c-Met, either directly, i.e., by interacting with c-Met itself, or indirectly, i.e., by interacting with another molecule on which the catalytic activity of c-Met is dependent. Such "contacting" can be accomplished in vitro, i.e., in a test tube, a Petri dish or the like. In a test tube, contacting may involve only a compound and c-Met or it may involve whole cells. Cells may also be maintained or grown in cell culture dishes and contacted with a compound in that environment. In this context, the ability of a particular compound to affect a c-Met related disorder, i.e., the $IC_{50}$ of the compound, defined below, can be determined before use of the compounds in vivo with more complex living organisms is attempted. For cells outside the organism, multiple methods exist, and are well-known to those skilled in the art, to get c-Met in contact with the compounds including, but not limited to, direct cell microinjection and numerous transmembrane carrier techniques.

"In vitro" refers to procedures performed in an artificial environment such as, e.g., without limitation, in a test tube or culture medium. The skilled artisan will understand that, for example, isolated c-Met may be contacted with a modulator in an in vftro environment. Alternatively, an isolated cell may be contacted with a modulator in an in vitro environment.

As used herein, "in vivo" refers to procedures performed within a living organism such as, without limitation, a mouse, rat, rabbit, ungulate, bovine, equine, porcine, canine, feline, primate, or human.

As used herein, "c-Met related disorder," refers to a condition characterized by inappropriate, i.e., under-activity or, more commonly, over-activity of the c-Met catalytic activity. A "c-Met related disorder" also refers to a condition where there may be a mutation in the gene that produces c-Met, which, in turn, produces a c-Met that has an increased or decreased c-Met catalytic activity. Inappropriate catalytic activity can arise as the result of either: (1) c-Met expression in cells which normally do not express c-Met, (2) increased c-Met expression leading to unwanted cell proliferation, differentiation and/or growth, or, (3) decreased c-Met expression leading to unwanted reductions in cell proliferation, differentiation and/or growth. Over-activity of a c-Met refers to either amplification of the gene encoding a c-Met or production of a level of c-Met activity which can correlate with a cell proliferation, differentiation and/or growth disorder (that is, as the level of the c-Met increases, the severity of one or more of the symptoms of the cellular disorder increases). Under-activity is, of course, the converse, wherein the severity of one or more symptoms of a cellular disorder increase as the level of the c-Met activity decreases.

As used herein, the terms "prevent", "preventing" and "prevention" refer to a method for barring an organism from acquiring a c-Met related disorder in the first place.

As used herein, the terms "treat", "treating" and "treatment" refer to a method of alleviating or abrogating a c-Met mediated cellular disorder and/or its attendant symptoms. With regard particularly to cancer, these terms simply mean that the life expectancy of an individual affected with a cancer will be increased or that one or more of the symptoms of the disease will be reduced.

The term "organism" refers to any living entity comprised of at least one cell. A living organism can be as simple as, for example, a single eukaryotic cell or as complex as a mammal. In a preferred aspect, the organism is a mammal. In a particularly preferred aspect, the mammal is a human being.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

By "monitoring" is meant observing or detecting the effect of contacting a compound with a cell expressing a c-Met. The observed or detected effect can be a change in cell phenotype, in the catalytic activity of c-Met or a change in the interaction of c-Met with a natural binding partner. Techniques for observing or detecting such effects are well-known in the art. For example, the catalytic activity of c-Met may be observed by determining the rate or amount of phosphorylation of a target molecule.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

A "natural binding partner" refers to a polypeptide that binds to a c-Met in a cell. Natural binding partners can play a role in propagating a signal in a c-Met-mediated signal transduction process. A change in the interaction of the natural binding partner with c-Met can manifest itself as an increased or decreased concentration of the c-Met/natural binding partner complex and, as a result, in an observable change in the ability of c-Met to mediate signal transduction.

As used herein, "administer" or "administration" refers to the delivery of a compound or salt of the present invention or of a pharmaceutical composition containing a compound or salt of this invention to an organism for the purpose of prevention or treatment of a c-Met-related disorder.

A "pharmaceutical composition" refers to a mixture of one or more of the compounds described herein, or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts, which retain the biological effectiveness and properties of the parent compound. Such salts include:

(1) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compounds of Formula (I) may also act as prodrugs. A "prodrug" refers to an agent, which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention, which is, administered as an ester (the "prodrug"), carbamate or urea.

Indications

A precise understanding of the mechanism by which the compounds of the invention, in particular, the compounds generated in vivo from the compounds of the invention, inhibit c-Met is not required in order to practice the present invention. However, while not hereby being bound to any particular mechanism or theory, it is believed that the compounds interact with the amino acids in the catalytic region of c-Met. The compounds disclosed herein may thus have utility as in vitro assays for such proteins as well as exhibiting in vivo therapeutic effects through interaction with such proteins.

In another aspect, this invention relates to a method for treating or preventing a c-Met related disorder by administering a therapeutically effective amount of a compound of this invention, or a salt thereof, to an organism.

It is also an aspect of this invention that a pharmaceutical composition containing a compound of this invention, or a salt thereof, is administered to an organism for the purpose of preventing or treating a c-Met related disorder.

This invention is therefore directed to compounds that modulate PK signal transduction by affecting the enzymatic activity of c-Met, thereby interfering with the signal transduced by c-Met. More particularly, the present invention is directed to compounds which modulate c-Met mediated signal transduction pathways as a therapeutic approach to treat the many cancers described herein.

A method for identifying a chemical compound that modulates the catalytic activity of c-Met is another aspect of this invention. The method involves contacting cells expressing c-Met with a compound of this invention (or its salt) and monitoring the cells for any effect that the compound has on them. Alternatively, the method can involve contacting the c-Met protein itself (i.e., not in a cell) with a chemical compound of the preferred embodiments of the present invention and monitoring the protein for any effect that the compound has on it. The effect may be observable, either to the naked eye or through the use of instrumentation. The effect may be, for example, a change or absence in a cell phenotype. The change or absence of change in the cell phenotype monitored, for example, may be, without limitation, a change or absence of change in the catalytic activity of c-Met in the cells or a change or absence of change in the interaction of c-Met with a natural binding partner.

Pharmaceutical Compositions and Use

A compound of the present invention or a physiologically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

Routes of Administration

Suitable routes of administration may include, without limitation, oral, intraoral, rectal, transmucosal or intestinal administration or intramuscular, epicutaneous, parenteral, subcutaneous, transdermal, intramedullary, intrathecal, direct intraventricular, intravenous, intravitreal, intraperitoneal, intranasal, intramuscular, intradural, intrarespiratory, nasal inhalation or intraocular injections. The preferred routes of administration are oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Composition/Formulation

Pharmaceutical compositions of the present invention may be manufactured by processes well known in the art, e.g., by means of conventional mixing, dissolving, granulating, dragee-making, levigating, emulsifying, encapsulating, entrapping, lyophilizing processes or spray drying.

Pharmaceutical compositions for use in the methods of the present invention may be prepared by any methods of pharmacy, but all methods include the step of bringing in association the active ingredient with the carrier which constitutes one or more necessary ingredients. In particular, pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

Dosage forms include tablets, troches, dispersions, suspensions, solutions, capsules, patches, syrups, elixirs, gels, powders, magmas, lozenges, ointments, creams, pastes, plasters, lotions, discs, suppositories, nasal or oral sprays, aerosols and the like.

For injection, the compounds of the invention may be formulated in aqueous solutions, preferably in physiologically compatible buffers such buffers with or without a low concentration of surfactant or cosolvent, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono- di- or triglycerides. Stabilizers may be added in these formulations, also.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, maleate, succinate, malate, acetate and methylsulfonate ($CH_3SO_3$), wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide ($Ca(OH)_2$), etc.).

Dosage

Pharmaceutical compositions suitable for use in the present invention include compositions wherein the active ingredients are contained in an amount sufficient to achieve the intended purpose, i.e., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of c-Met activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50–90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

EXAMPLES

Scheme I. General Synthetic Scheme

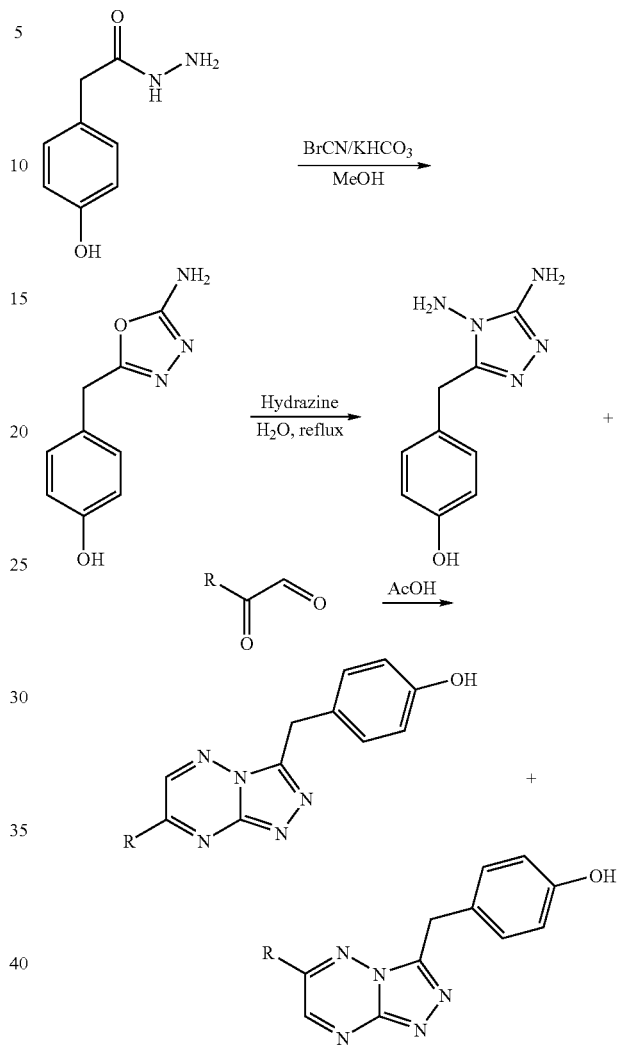

(4-Hydroxy-phenyl)-acetic acid hydrazide

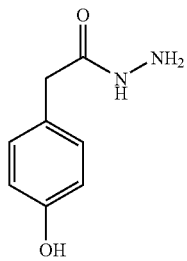

Neat anhydrous hydrazine 21.0 g (654 mmol) was added to a solution of p-hydroxyphenylacetic acid methyl ester 27.18 g (163.5 mmol) in MeOH (100 mL) and the mixture was heated to 50–55° C. and stirred at this temperature for 90 min (water bath). Cooled, stirred for extra 1 hour, the precipitate collected by filtration, compressed on the frit, washed with MeOH (3×10 mL) and dried on high vacuum. A second fraction was obtained by cooling the supernatants to −15° C. overnight and filtering the formed precipitate. Combined yield: 25.13 g of a white cryst. solid (92.5%).

$^1$H-NMR(DMSO-d$_6$, 400 MHz): 9.182 (br s, 1H), 9.108 (br s, 1H), 7.035 (app d, J=8.6 Hz, 2H), 6.666 (app d, J=8.6 Hz, 2H), 4.176 (br d, j=3.1 Hz, 2H), 3.207 (s, 2H); $^{13}$C-NMR (DMSO-d$_6$, 100 MHz): 170.66, 156.45, 130,47(2C), 127.00, 115.63 (2C), 40.48

4-(5-Amino-[1,3,4]oxadiazol-2-ylmethyl)-phenol

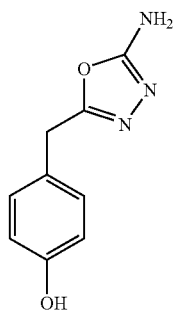

Solid BrCN 6.059 g (57.2 mmol) was added in one portion into ice-cooled slurry of (4-hydroxy-phenyl)-acetic acid hydrazide 8.642 g (52.0 mmol) and KHCO$_3$ 6.510 g (65 mmol) in MeOH (100 mL). The mixture was stirred at 0–5° C. for 1 hour, the ice bath allowed to melt and stirred at R.T. overnight (18 hr). The reaction mixture was diluted with water (100 mL), stirred for 1 hour, the precipitate was collected by filtration, washed with water and dried on high vacuum. A second fraction precipitated after concentrating and cooling the supernatants. Combined yield: 9.018 g (90.5%) of a white cryst. solid. $^1$H-NMR(DMSO-d$_6$, 400 MHz): 9.334 (s, 1H) 7.040 (app d, J=9.0 Hz, 2H), 6.839 (br s, 2H), 6.706 (app d, J=8.6 Hz, 2H), 3.879 (s, 2H)

4-(4,5-Diamino-4H-[1,2,4]triazol-3-ylmethyl)-phenol

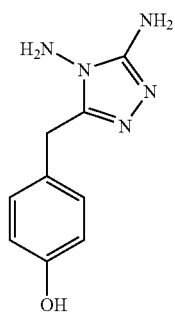

A mixture of 4-(5-amino-[1,3,4]oxadiazol-2-ylmethyl)-phenol 4.902 g (25.64 mmol), water 40 mL and anhydrous hydrazine 13 mL was refluxed on an oil bath (190° C.) for 18 hours. The mixture was cooled, allowed to crystallize at R.T. for 2hours, then placed into a freezer (−20° C.) overnight (16 hrs). The precipitated product was collected by filtration, washed with chilled MeOH (−15° C.) and dried on high vacuum. The crude product was re-crystallized from water (80 mL, reflux to +4° C. overnight). Filtered, washed with ice-cold water and dried on high vacuum. Y=1.658 g (31.5%) of a white cryst. solid. MS+cAPCI: 206(M+1); MS-cAPCI: 204,202(M−1); $^1$H-NMR(DMSO-d$_6$, 400 MHz): 9.234 (br s, 1H), 7.034 (app d, J=8.6 Hz, 2H), 6.664 (app d, J=8.6 Hz, 2H), 5.453 (br s, 2H), 5.338 (s, 2H), 3.772 (s, 2H)

(4-Fluoro-phenyl)-acetic acid hydrazide

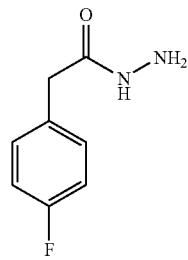

Neat anh. hydrazine 20 mL was added to a slurry of (4-fluorophenyl)acetic acid methyl ester (Acros Organics USA, Morris Plains, N.J., 25.66 g, 152.5 mmol) in MeOH (120 mL) and the mixture was heated to 60° C. with reflux condenser under nitrogen for 2 hrs. Cooled to R.T., evaporated to dryness (R.T. to 60° C., 100 Torr to 7 Torr). The solid residue was re-crystallized from 1-propanol , 100 mL (reflux to R.T., overnight). The cryst. product was collected by filtration, washed with 1-propanol and dried on high vacuum. [1$^{st}$ fraction]. Evaporating the supernatants to dryness on high vacuum, the obtained solid residue was dried on high vacuum overnight. The residue was then re-crystallized from benzene. (reflux to R.T., overnight) The precipitated product was collected by filtration, washed with a mixture benzene-hexane (1:1), then with hexane. Dried on high vacuum. [2$^{nd}$ fraction]. Combined yield: 24.855 g of a white cryst. flakes (97%). $^1$H-NMR(DMSO-d$_6$, 400 MHz): 9.194 (br s, 1H), 7.272 (m, 2H), 7.107 (m, 2H), 4.202 (br d, J=4.3 Hz, 2H), 3.329 (s, 2H); $^{19}$F-NMR(DMSO-d$_6$, 376.5 MHz): −116.96 (m, 1F).

5-(4-Fluoro-benzyl)-[1,3,4]oxadiazol-2-ylamine

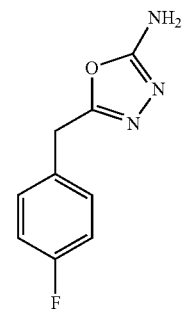

Solid BrCN 13.37 g (130 mmol, 1.1 eq.) was added in one portion into ice-cooled slurry of (4-Fluoro-phenyl)-acetic acid hydrazide (19.85 g, 118 mmol) and KHCO3 14.77 g (147.5 mmol, 1.25 eq) in MeOH (150 mL) in a 1L flask. (Followed by MeOH 10 mL to wash the funnel). The mixture was stirred on ice bath at 0–5° C. for 2 hours in a loose-capped flask, then the bath allowed to melt gradually and then the mixture was stirred at 5 to 20° C. overnight (17 hrs). The reaction mixture was diluted with water (200 mL), stirred for 1 hour in an open flask, then cooled on ice bath. The precipitate was collected by filtration, washed with water and dried on highvac. [1$^{st}$ fraction] The supernatants were concentrated on rotavap form warm (40° C.) water bath to remove all MeOH and some water. The obtained slurry was cooled to R.T., the precipitate was collected by filtration, washed with water and dried on highvac. [2$^{nd}$ fraction]. Combined yield: 20.836 g (91.5%) of a white cryst. solid. $^1$H-NMR(DMSO-d$_6$, 400 MHz): 7.289 (m, 2H), 7.148 (m, 2H), 6.873 (br s, 2H), 4.014 (s, 2H); $^{19}$F-NMR (DMSO-d$_6$, 376.5 MHz): 116.01 (m, 1F).

5-(4-Fluoro-benzyl)-[1,2,4]triazole-3,4-diamine

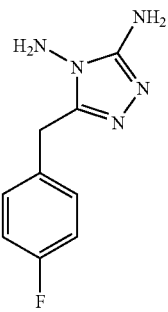

A mixture of 5-(4-fluoro-benzyl)-[1,3,4]oxadiazol-2-ylamine 10.182 g (52.7 mmol), water 80 mL and anhydrous hydrazine 20 mL was refluxed under nitrogen on an oil bath (190–200 °C.) for 23 hours. The mixture was cooled and allowed to crystallize at R.T. under nitrogen overnight. The precipitated product was collected by filtration, washed with ice-cold water (10 mL) and dried on high vacuum. The crude product was re-crystallized from water 60 mL (reflux under nitrogen, than to +4° C. in a refrigerator overnight). The product was filtered, washed with ice-cold water and dried on high vacuum. Y=6.210 g (56.5%) of a large white crystals. $^1$H-NMR(DMSO-$d_6$, 400 MHz): 7.267 (app d, J=8.6 Hz, J=5.5 Hz, 2H), 7.097 (app t, J=9.0 Hz, 2H), 5.509 (br s, 2H), 5.339 (s, 2H), 3.884 (s, 2H); $^{19}$F-NMR(DMSO-$d_6$, 376.5 MHz): −117.14 (m, 1F).

Example 1

4-[6-(4-Fluoro-phenyl)-[1,2,4]triazolo[4,3-b][1,2,4]triazin-3-ylmethyl]-phenol

General Procedure A: a mixture of (4-fluoro-phenyl)-oxo-acetaldehyde (72 mg, 0.4 mmol) and

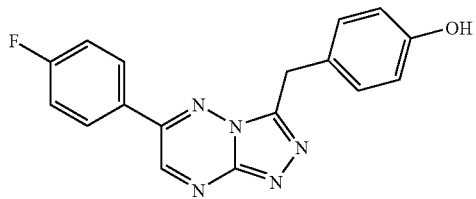

4-(4,5-diamino-4H-[1,2,4]triazol-3-ylmethyl)-phenol (82 mg, 0.4 mmol) in acetic acid was stirred at room temperature overnight. The solvent was removed under reduced pressure and the residue was purified on a silica gel column (CH2Cl2:EtOAc=2:8, 3:7) to afford two isomers 4-[7-(4-fluoro-phenyl)-[1,2,4]triazolo[4,3-b][1,2,4]triazin-3-ylmethyl]-pheno desired product 4-[6-(4-fluoro-phenyl)-[1,2,4]triazolo[4,3-b][1,2,4]triazin-3-ylmethyl ]phenol (Example 1).

4-[7-(4-fluoro-phenyl)-[1,2,4]triazolo[4,3-b][1,2,4]triazin-3-ylmethyl]-phenol: yellow solid (67 mg, 52%). $^1$H-NMR (400 MHz, DMSO-$d_6$) δ 9.39 (s, 1H), 9.27 (s, 1H), 8.37 (m, 2H) 7.46 (m, 2H), 7.11 (d, J=8.2 Hz, 2H), 6.66 (d, J=8.6 Hz, 2H), 4.38 (s, 2H). MS (m/z) 322 [M+1]. Example 1: light yellow solid (23 mg, 18%). $^1$H-NMR (400 MHz, DMSO-$d_6$) δ 9.30 (s, 1H), 9.27 (s, 1H), 8.22 (m, 2H), 7.47 (m, 2H), 7.17 (d, J=8.6 Hz, 2H), 6.68 (d, J=8.6 Hz, 2H), 4.41 (s, 2H). MS (m/z) 322 [M+1].

Example 2

4-(6-Thiophen-2-yl-[1,2,4]triazolo[4,3-b][1,2,4]triazin-3-ylmethyl)-phenol

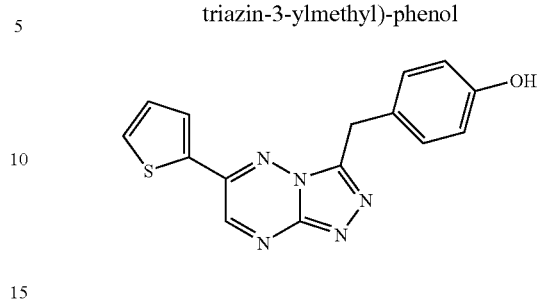

General procedure A was followed with the reaction of oxo-thiophen-2-yl-acetaldehyde and 4-(4,5-diamino-4H-[1,2,4]triazol-3-ylmethyl)-phenol to provide 4-(7-thiophen-2-yl-[1,2,4]triazolo[4,3-b][1,2,4]triazin-3-ylmethyl)-phenol and the desired product 4-(6-thiophen-2 -yl[1,2,4]triazolo[4,3-b][1,2,4]triazin-3-ylmethyl)-phenol (example 2).

4-(7-thiophen-2-yl-[1,2,4]triazolo[4,3-b][1,2,4]triazin-3-ylmethyl)-phenol: yellow solid (39%).

$^1$H-NMR (400 MHz, DMSO-$d_6$) δ 9.33 (s, 1H), 9.26 (s, 1H), 8.31 (d, 1H), 8.02 (d, 1H), 7.33 (m, 1H), 7.10 (d, 2H), 6.66 (d, 2H), 4.34 (s, 2H). MS (m/z) 310 [M+1].

Example 2: light yellow solid (7%). $^1$-NMR (400 MHz, DMSO-$d_6$) δ 9.31 (s, 1 H), 9.26 (s, 1H), 8.23 (d, 1H), 7.93 (d, 1H), 7.30 (m, 1H), 7.16 (d, 2H), 6.66 (d, 2H), 4.34 (s, 2H). MS (m/z) 310 [M+1].

Example 3

4-(6-Phenyl-[1,2,4]triazolo[4,3-b][1,2,4]triazin-3-ylmethyl)-phenol

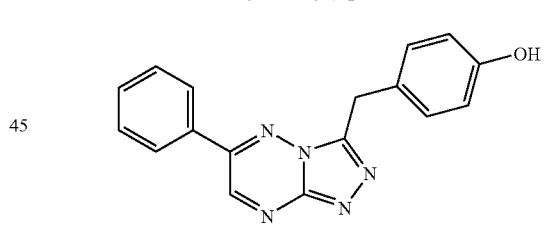

General procedure A was followed with the reaction of oxo-phenyl-acetaldehyde and 4-(4,5-diamino-4H-[1,2,4]triazol-3-ylmethyl)-phenol to provide 4-(7-phenyl-[1,2,4]triazolo[4,3-b][1,2,4]triazin-3-ylmethyl)-phenol and the desired product 4-(6-phenyl-[1,2,4]triazolo[4,3-b][1,2,4]triazin-3-ylmethyl)-phenol (example 3).

4-(7-phenyl-[1,2,4]triazolo[4,3-b][1,2,4]triazin-3-ylmethyl)-phenol: yellow solid (63%)$^1$H-NMR (400 MHz, DMSO-$d_6$) δ 9.40 (s, 1H), 9.27 (s, 1H), 8.29 (m, 2H), 7.62 (m, 3H), 7.11 (d, J=8.6 Hz, 2H), 6.66 (d, J=8.6 Hz, 2H), 4.38 (s, 2H). MS (m/z) 304 [M+1].

Example 3: light yellow solid (14%). $^1$H-NMR (400 MHz, DMSO-$d_6$) δ 9.31 (s, 1H), 9.26 (s, 1H), 8.15 (m, 2H), 7.62 (m, 3H), 7.17 (d, J=8.6 Hz, 2H), 6.67 (d, J=8.6 Hz, 2H, 4.42 (s 2H). MS (m/z) 304 [M+1].

Example 4

3-(4-Fluoro-benzyl)-6-phenyl-[1,2,4]triazolo[4,3-b][1,2,4]triazine

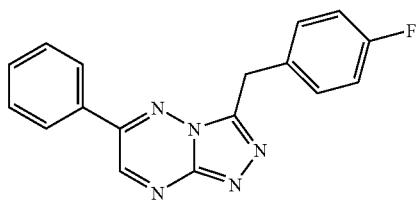

General procedure A was followed with the reaction of oxo-phenyl-acetaldehyde and 5-(4-fluoro-benzyl)-[1,2,4]triazole-3,4-diamine to provide 3-(4-fluoro-benzyl)-7-phenyl-[1,2,4]triazolo[4,3-b][1,2,4]triazine and the desired product 3-(4-fluoro-benzyl)-6-phenyl-[1,2,4]triazolo[4,3-b][1,2,4]triazine (example 4).

3-(4-Fluoro-benzyl)-7-phenyl-[1,2,4]triazolo[4,3-b][1,2,4]triazine: yellow solid (68%). $^1$H-NMR (400 MHz, DMSO-$d_6$) δ 9.41 (s, 1H), 8.32 (m, 2H), 7.63 (m, 3H), 7.37 (m, 2H), 4.52 (s, 2H). MS (m/z) 306 [M+1].

Example 4: light yellow solid (20%). $^1$H-NMR (400 MHz, DMSO-$d_6$) δ 9.33 (s, 1H), 8.15 (m, 2H), 7.62 (m, 3H), 7.42 (m, 2H), 7.14 (m, 2H), 4.56 (s, 2H). MS (m/z) 306 [M+1].

Example 5

3-(4-Fluoro-benzyl)-6-thiophen-2-yl-[1,2,4]triazolo[4,3-b][1,2,4]triazine

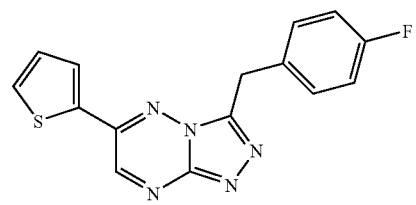

General procedure A was followed with the reaction of oxo-thiophen-2-yl-acetaldehyde and 5-(4-fluoro-benzyl)-[1,2,4]triazole-3,4-diamine to provide 3-(4-fluoro-benzyl)-7-thiophen-2-yl-[1,2,4]triazolo[4,3-b][1,2,4]triazine and 3-(4-fluoro-benzyl)-6-thiophen-2-yl-[1,2,4 ][triazolo 1,2,4,-b][1,2,4]triazine (example 5).

3-(4-Fluoro-benzyl)-7-thiophen-2-yl-[1,2,4]triazolo[4,3-b][1,2,4]triazine: yellow solid (76%). $^1$H-NMR (400 MHz, DMSO-$d_6$) δ 9.34 (s, 1H), 8.32 (d, 1H), 8.02 (d, 1H), 7.34 (m, 3H), 2H), 4.47 (s, 2H). MS (m/z) 310 [M+1].

Example 5: yellow solid (9%). $^1$H-NMR (400 MHz, DMSO-$d_6$) δ 9.33 (s, 1H), 8.24 (d, 1H), 7.41 (m, 2H), 7.30 (m, 1H), 7.13 (m, 2H), 4.48 (s, 2H). MS (m/z) 310 [M+1].

Example 6

6-(4-Bromo-phenyl)-3-(4-fluoro-benzyl)-[1,2,4]triazolo[4,3-b][1,2,4]triazine

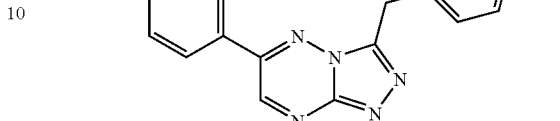

General procedure A was followed with the reaction of (4-bromo-phenyl)-oxo-acetaldehyde and 5-(4-fluoro-benzyl)-[1,2,4]triazole-3,4-diamine to provide 7-(4-bromo-phenyl)-3-(4-fluoro-benzyl)-[1,2,4]triazolo[4,3-b][1,2,4]triazine and 6-(4-bromo-phenyl)-3-(4-fluoro-benzyl)-[1,2,4]triazolo[4,3-b][1,2,4]triazine (example 5).

7-(4-Bromo-phenyl)-3-(4-fluoro-benzyl )-[1,2,4]triazolo[4,3-b][1,2,4]triazine: yellow solid (30%).

$^1$H-NMR (400 MHz, DMSO-$d_6$) δ 9.40 (s, 1 H), 8.25 (d, 2H), 7.83 (d, 2H), 7.36 (m, 2H), 7.15 (m, 2H), 4.52 (s, 2H). MS (m/z) 384 [M+1].

Example 6: light yellow solid (61%). $^1$H-NMR (400 MHz, DMSO-$d_6$) δ 9.32 (s, 1H), 8.10 (d 2H), 7.83 (d, 2H), 7.42 (m, 2H), 7.16 (m, 2H), 4.55 (s, 2H). MS (m/z) 384 [M+1).

Example 7

4-[1,2,4]Triazolo[4,3-b][1,2,4]triazin-3-ylmethyl-phenol

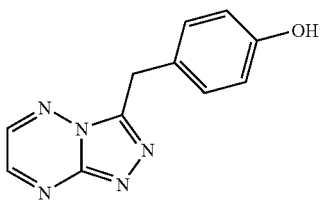

General procedure A was followed with the reaction of ethanedial and 4-(4,5-diamino-4H-[1,2,4]triazol-3-ylmethyl)-phenol to provide 4-[1,2,4]triazolo[4,3-b][1,2,4]triazin-3-ylmethyl-phenol (example 7).

$^1$H-NMR (400 MHz, DMSO-$d_6$) δ 9.25 (s, 1 H), 8.68 (d, 2H), 7.16 (m, 2H), 6.65 (m, 2H), 4.35 (s, 2H). MS (m/z) 228 [M+1].

Example 8

4-(6,7-Dimethyl-[1,2,4]triazolo[4,3-b][1,2,4]triazin-3-ylmethyl)-phenol

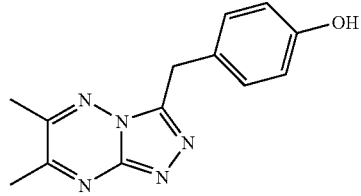

General procedure A was followed with the reaction of butane-2,3-dione and 4-(4,5-diamino-4H-[1,2,4]triazol-3-ylmethyl)-phenol to provide 4-(6,7-dimethyl-[1,2,4]triazolo[4,3-b][1,2,4]triazin-3-ylmethyl)-phenol (example 8).
$^1$H-NMR (400 MHz, DMSO-$d_6$) δ 9.25 (s, 1H), 7.12 (m, 2H), 6.65 (m, 2H), 4.30 (s, 2H), 2.58 (s, 3H), 2.50 (s, 3H). MS (m/z) 256 [M+1].

Example 9

3-(4-Hydroxy-benzyl)-6-methyl-[1,2,4]triazolo[4,3-b][1,2,4]triazin-7-ol

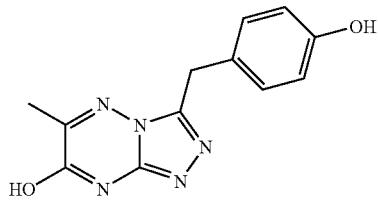

General procedure A was followed with the reaction of 2-oxo-propionic acid methyl ester and 4-(4,5-diamino-4H-[1,2,4]triazol-3-ylmethyl)-phenol to provide 3-(4-hydroxy-benzyl)-6-methyl-1,2,4]triazolo[4,3-b][1,2,4]triazin-7-ol.
$^1$H-NMR (400 MHz, DMSO-$d_6$) δ 9.26 (s, 1H), 7.10 (d, 2H), 6.65 (d, 2H), 4.05 (s, 2H), 2.22 (s 3H). MS (m/z) 258 [M+1].

Example 10

4-(7-Chloro-6-methyl-[1,2,4]triazolo[4,3-b][1,2,4]triazin-3-ylmethyl)-phenol

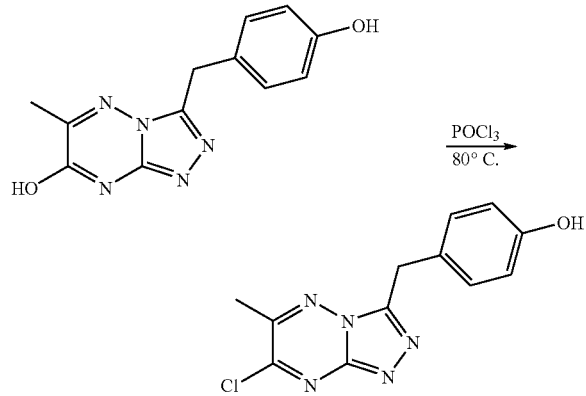

A solution of 3-(4-hydroxy-benzyl)-6-methyl-[1,2,4]triazolo[4,3-b][1,2,4]triazin-7-ol (170 mg, 0.62 mmol) in POCl$_3$ (5 mL) was heated at 80° C. for 15 minutes, and then POCl$_3$ was evaporated. The residue was purified on a silica gel column eluting with 5% methanol in dichloromethane to provide 4-(7-chloro-6-methyl-[1,2,4]triazolo[4,3-b][1,2,4]triazin-3-ylmethyl)-phenol (80 mg). MS (m/z) 275 [M+1].

Example 11

4-(7-Amino-6-methyl-[1,2,4]triazolo[4,3-b][1,2,4]triazin-3-ylmethyl)-phenol

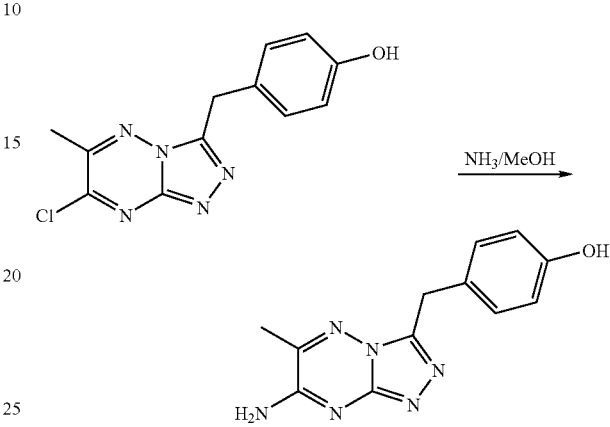

NH$_3$ gas was bubbled through a solution of 4-(7-chloro-6-methyl-[1,2,4]triazolo[4,3-b][1,2,4]triazin-3-ylmethyl)-phenol (70 mg, 0.25 mmol) in methanol (5 mL) at 0° C. The saturated solution was stirred at 70° C. until the starting material disappeared. After evaporation of solvent, the residue was purified on a silica gel column eluting with 10% methanol in dichloromethane to provide 4-(7-amino-6-methyl-[1,2,4]triazolo[4,3-b][1,2,4]triazin-3-ylmethyl)-phenol (35 mg). $^1$H-NMR (400 MHz, DMSO-$d_6$) δ 9.22 (s, 1H), 7.05 (d, 2H), 6.65 (d, 2H), 4.12 (s, 2H), 2.35 (s, 3H). MS (m/z) 257 [M+1].

Biological Examples

The following assays are employed to find those compounds demonstrating the optimal degree of the desired activity.

A. Assay Procedures.

The following assays may be used to determine the level of activity and effect of the different compounds of the present invention on one or more of the PKs. Similar assays can be designed along the same lines for any PK using techniques well known in the art.

Several of the assays described herein are performed in an ELISA (Enzyme-Linked Immunosorbent Sandwich Assay) format (Voller, et al., 1980, "Enzyme-Linked Immunosorbent Assay," Manual of Clinical Immunology, 2d ed., Rose and Friedman, Am. Soc. Of Microbiology, Washington, D.C., pp. 359–371). The general procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The presently preferred protocols for conducting the ELISA experiments for specific PKs is provided below. However, adaptation of these protocols for determining the activity of compounds against other RTKs, as well as for CTKs and STKs, is well within the scope of knowledge of those skilled in the art. Other assays described herein measure the amount of DNA made in response to activation of a test kinase, which is a general measure of a proliferative response. The general procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as 5-bromodeoxyuridine (BrdU) or $H^3$-thymidine is added. The amount of labeled DNA is detected with either an anti-BrdU antibody or by measuring radioactivity and is compared to control cells not contacted with a test compound.

Met Transphorylation Assay

This assay is used to measure phosphotyrosine levels on a poly(glutamic acid:tyrosine (4:1)) substrate as a means for identifying agonists/antagonists of met transphosphorylation of the substrate.

Materials and Reagents:
1. Corning 96-well Elisa plates, Corning Catalog # 25805-96.
2. Poly(glu, tyr) 4:1, Sigma, Cat. No; P 0275.
3. PBS, Gibco Catalog # 450–1300EB
4. 50 mM HEPES
5. Blocking Buffer: Dissolve 25 g Bovine Serum Albumin, Sigma Cat. No A-7888, in 500 ml PBS, filter through a 4 μm filter.
6. Purified GST fusion protein containing the Met kinase domain, Sugen, Inc.
7. TBST Buffer.
8. 10% aqueous (MilliQue $H_2O$) DMSO.
9. 10 mM aqueous (d$H_2O$) Adenosine-5'-triphosphate, Sigma Cat. No. A-5394.
10. 2× Kinase Dilution Buffer: for 100 ml, mix 10 mL 1M HEPES at pH 7.5 with 0.4 mL 5% BSA/PBS, 0.2 mL 0.1 M sodium orthovanadate and 1 mL 5M sodium chloride in 88.4 mL d$H_2O$.
11. 4× ATP Reaction Mixture: for 10 mL, mix 0.4 mL 1 M manganese chloride and 0.02 mL 0.1 M ATP in 9.56 mL d$H_2O$.
12. 4× Negative Controls Mixture: for 10 mL, mix 0.4 mL 1 M manganese chloride in 9.6 mL d$H_2O$.
13. NUNC 96-well V bottom polypropylene plates, Applied Scientific Catalog # S-72092
14. 500 mM EDTA.
15. Antibody Dilution Buffer: for 100 mL, mix 10 mL 5% BSA/PBS, 0.5 mL 5% Carnation Instant Milk® in PBS and 0.1 mL 0.1 M sodium orthovanadate in 88.4 mL TBST.
16. Rabbit polyclonal antophosphotyrosine antibody, Sugen, Inc.
17. Goat anti-rabbit horseradish peroxidase conjugated antibody, Biosource, Inc.
18. ABTS Solution: for 1 L, mix 19.21 g citric acid, 35.49 g $Na_2HPO_4$ and 500 mg ABTS with sufficient d$H_2O$ to make 1 L.
19. ABTS/$H_2O_2$: mix 15 mL ABST solution with 2pL $H_2O_2$ five minutes before use.
20. 0.2 M HCl Procedure:
1. Coat ELISA plates with 2 μg Poly(Glu—Tyr) in 100 μL PBS, store overnight at 4° C.
2. Block plate with 150 μL of 5% BSA/PBS for 60 min.
3. Wash plate twice with PBS, once with 50 mM Hepes buffer pH 7.4.
4. Add 50 μl of the diluted kinase to all wells. (Purified kinase is diluted with Kinase Dilution Buffer. Final concentration should be 10 ng/well.)
5. Add 25 μL of the test compound (in 4% DMSO) or DMSO alone (4% in d$H_2O$) for controls to plate.
6. Incubate the kinase/compound mixture for 15 minutes.
7. Add 25 μL of 40 mM $MnCl_2$ to the negative control wells.
8. Add 25 μL ATP/$MnCl_2$ mixture to the all other wells (except the negative controls). Incubate for 5 min.
9. Add 25 μL 500 mM EDTA to stop reaction.
10. Wash plate 3× with TBST.
11. Add 100 μL rabbit polyclonal anti-Ptyr diluted 1:10,000 in Antibody Dilution Buffer to each well. Incubate, with shaking, at room temperature for one hour.
12. Wash plate 3× with TBST.
13. Dilute Biosource HRP conjugated anti-rabbit antibody 1:6,000 in Antibody Dilution buffer. Add 100 μL per well and incubate at room temperature, with shaking, for one hour.
14. Wash plate 1× with PBS.
15. Add 100 μl of ABTS/$H_2O_2$ solution to each well.
16. If necessary, stop the development reaction with the addition of 100 μl of 0.2M HCl per well.
17. Read plate on Dynatech MR7000 Elisa reader with the test filter at 410 nM and the reference filter at 630 nM.

Met Transphosphorylation Assay Results

Table 1 shows the IC50 values obtained for a number of compounds of the preferred embodiments of the invention.

TABLE 1

| Example | Structure | c-MET IC$_{50}$ (μM) |
|---|---|---|
| 1 | (4-fluorophenyl and 4-hydroxybenzyl substituted triazolo-triazine structure) | <0.0091/0.020 |

TABLE 1-continued

| Example | Structure | c-MET IC$_{50}$ (µM) |
|---|---|---|
| 2 | 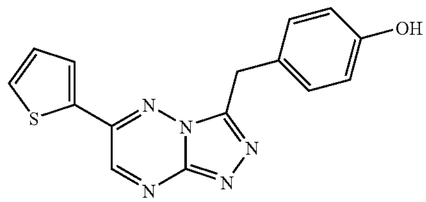 | 0.004 |
| 3 | 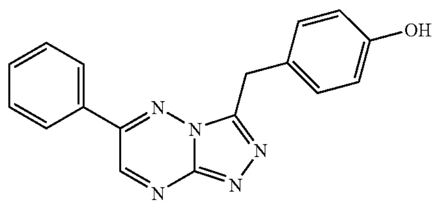 | 0.006 |
| 4 | 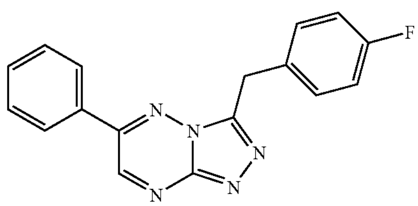 | 0.05 |
| 5 | 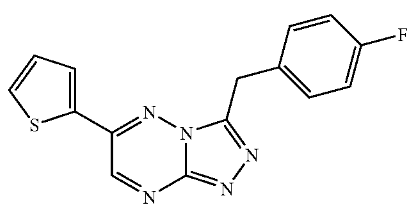 | 0.013 |
| 6 | 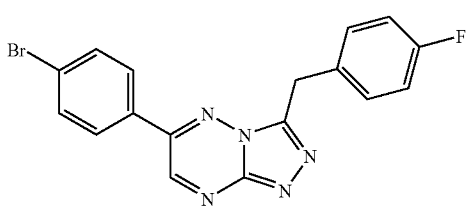 | 0.045 |
| 7 | 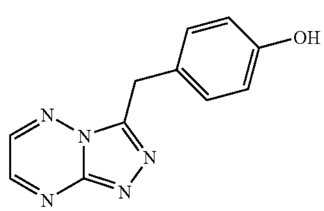 | 0.056 |
| 8 | 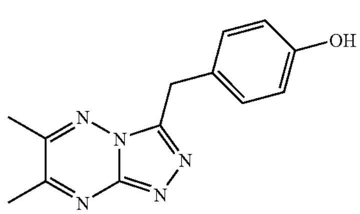 | >20 |

TABLE 1-continued

| Example | Structure | c-MET IC$_{50}$ (μM) |
|---|---|---|
| 9 | (structure) | 0.83 |

One skilled in the art would also readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, -are exemplary, and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X, being bromine and claims for X being bromine and chlorine are fully described.

TABLE 2

| Example | Structure | Name |
|---|---|---|
| 1 | (structure) | 4-[6-(4-Fluoro-phenyl)-[1,2,4]triazolo[4,3-b][1,2,4]triazin-3-ylmethyl]-phenol |
| 2 | (structure) | 4-(6-Thiophen-2-yl-[1,2,4]traizolo[4,3-b][1,2,4]traizin-3-ylmethyl)-phenol |

TABLE 2-continued

| Example | Structure | Name |
|---|---|---|
| 3 | 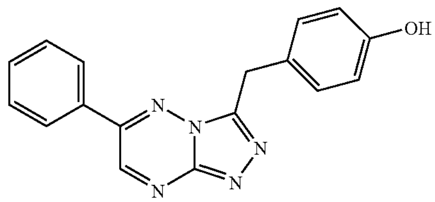 | 4-(6-Phenyl-[1,2,4]triazolo[4,3-b][1,2,4]triazin-3-ylmethyl)-phenol |
| 4 | 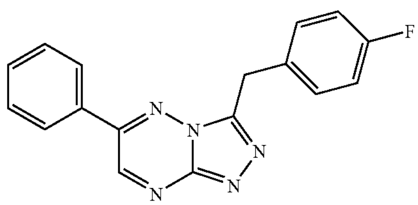 | 3-(4-Fluoro-benzyl)-6-phenyl-[1,2,4]triazolo[4,3-b][1,2,4]triazine |
| 5 | 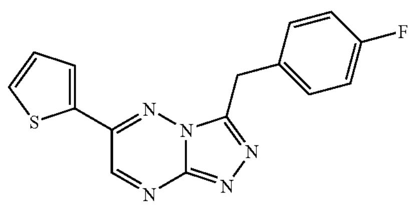 | 3-(4-Fluoro-benzyl)-6-thiophen-2-yl-[1,2,4]triazolo[4,3-b][1,2,4]triazine |
| 6 | 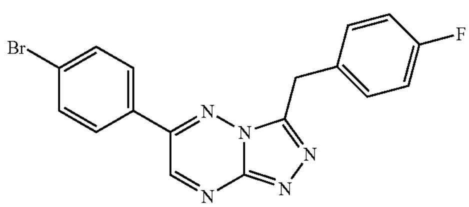 | 6-(4-Bromo-phenyl)-3-(4-fluoro-benzyl)-[1,2,4]triazolo[4,3-b][1,2,4]triazine |
| 7 | 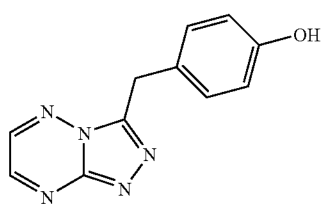 | 4-[1,2,4]Triazolo[4,3-b][1,2,4]triazin-3-ylmethyl-phenol |
| 8 | 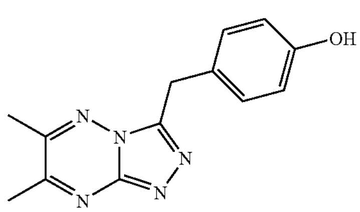 | 4-(6,7-Dimethyl-[1,2,4]triazolo[4,3-b][1,2,4]triazin-3-ylmethyl)-phenol |
| 9 | 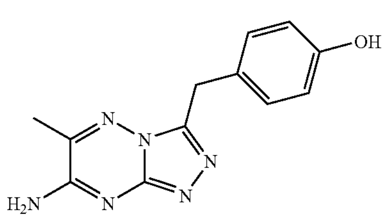 | 4-(7-Amino-6-methyl-[1,2,4]triazolo[4,3-b][1,2,4]triazin-3-ylmethyl)-phenol |

What is claimed is:

1. A compound of the Formula (I):

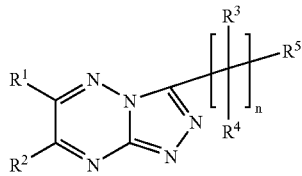

wherein:
n is 1, 2 or 3;
R¹ is selected from the group consisting of hydrogen, halogen, NR⁶R⁷, —CN, —COR⁶, —COOR⁶, —CONR⁶R⁷, perfluoroalkyl, $C_1$–$C_6$ alkyl, cycloalkyl, heterocycle, alkenyl, alkynyl, aryl, and heteroaryl, wherein the $C_1$–$C_6$ alkyl, cycloalkyl, heterocycle, alkenyl, alkynyl, aryl or heteroaryl of R¹ may be optionally and independently substituted with halogen, —OH, —OR⁶, —COR⁷, —CONR⁶R⁷, —COOR⁶, —NR⁶R⁷, —CN, —NO₂, —S(O)ₘR⁶, (m=0, 1 or 2), —S(O₂)NR⁶R⁷, —NR⁶ R⁷, perfluoroalkyl, $C_1$–$C_6$ alkyl, cycloalkyl, heterocycle, $C_1$–$C_6$ alkenyl, $C_1$–$C_6$ alkynyl, aryl, heteroaryl, —NR⁶ONR⁶R⁷, —NR⁶OR⁷ or —NR⁶S(O₂)R⁷;
R² is selected from the group consisting of hydrogen, halogen, $C_1$–$C_6$ alkyl, NR⁸R⁹, —CN, —COR⁸, —COOR⁹, —CO R⁸R⁹, and perfluoroalkyl;
each R³ and R⁴ is independently selected from the group consisting of hydrogen, halogen, —OH, —OR⁶, —NR⁶R⁷, —CN, —COR⁶, —COOR⁶, —CONR⁶R⁷, —NR⁶R⁷, perfluoroalkyl, $C_1$–$C_6$ alkyl, aryl, heterocycle and heteroaryl;
R⁵ is aromatic ring or heteroaromatic ring, wherein R⁵ is optionally substituted at one or more positions with halogen, —OH, —OR⁶, —COR⁷, —CONR⁶R⁷, —COOR⁶, —NR⁶R⁷, —CN, —NO₂, —S(O)ₘR⁶, (m=0, 1 or 2), —S(O)₂)NR⁶R⁷, —NR⁶R⁷, perfluoroalkyl or $C_1$–$C_6$ alkyl;
each R⁶ and R⁷ is independently selected from the group consisting of hydrogen, $C_1$–$C_6$ alkyl, cycloalkyl, heterocyclic, alkenyl, alkynyl, aryl, aminoalkyl, alkylaminoalkyl, and dialkylaminoalkyl; and
each R⁸ and R⁹ is independently selected from the cirouo consisting of hydrogen, and $C_1$–$C_6$ alkyl; or
a pharmaceutically acceptable salt thereof.

2. The compound of claim 1, wherein R¹ is aryl or heteroaryl, wherein the aryl or heteroaryl is optionally substituted at one or more positions with halogen, —OH, —OR⁶, —COR⁷, —CONR⁶R⁷, COOR⁶, —NR⁶R⁷, —CN, —NO₂, —S(O)ₘR⁶, (m=0, 1 or 2), —S(O₂)NR⁶R⁷, —NR⁶R⁷, perfluoroalkyl, $C_1$–$C_6$ alkyl, cycloalkyl, heterocycle, $C_1$–$C_6$ alkenyl, $C_1$–$C_6$ alkynyl, aryl, heteroaryl, —NR⁶ONR⁶R⁷, —NR⁶OR⁷ or —NR⁶S(O₂)R⁷.

3. The compound of claim 1, wherein the aryl or heteroaryl is a five or six membered ring.

4. The compound of claim 1, wherein R² is H or $C_1$–$C_6$ alkyl.

5. The compound of claim 4, wherein R² is H.

6. The compound of claim 1, wherein R⁵ is a 6 membered aryl or heteroaryl ring, wherein the 6 membered heteroaryl ring contains one or more heteroatoms selected from the group consisting of S, O and N.

7. The compound of claim 6, wherein the 6 membered heteroaryl ring contains one nitrogen.

8. The compound of claim 6, wherein R⁵ is selected from the group consisting of pyranyl, pyridyl, pyrazinyl, pyrimidinyl, or pyridazinyl.

9. The compound of claim 5, wherein R⁵ is phenyl and is optionally substituted with hydroxy or halo.

10. The compound of claim 1, wherein n is 1 or 2.

11. The compound of claim 1, wherein n is 1, R³ is H, and R⁴ is H.

12. A compound selecte from the group consisting of

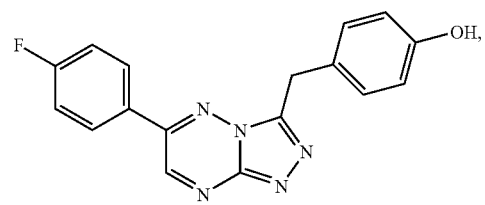

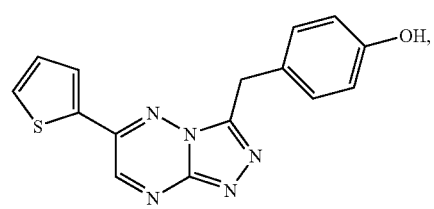

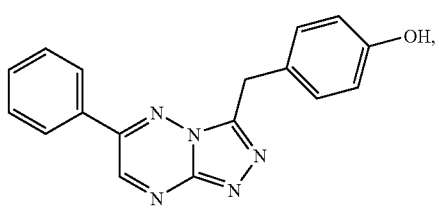

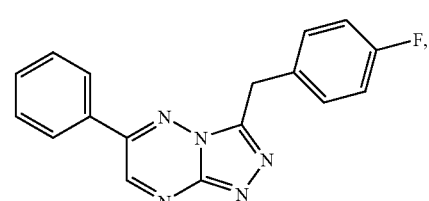

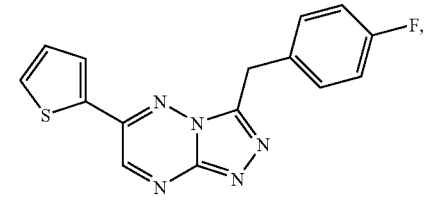

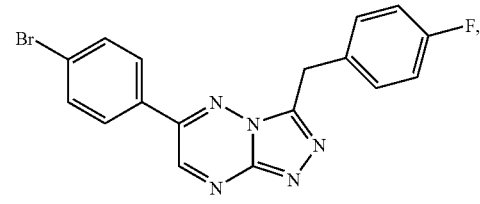

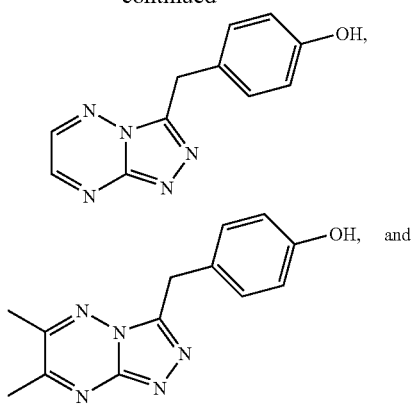
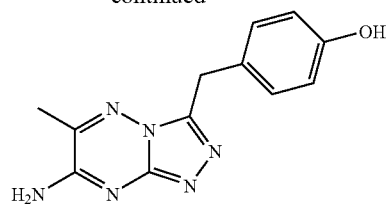
and
or a pharmaceutically acceptable salt thereof.
13. A pharmaceutically acceptable composition comprising a compound of claim 1, or a pharmaceutically acceptable salt thereof, and a pharmaceutically acceptable carrier.
* * * * *